US 6,660,476 B2

(12) United States Patent
Comings et al.

(10) Patent No.: US 6,660,476 B2
(45) Date of Patent: Dec. 9, 2003

(54) POLYMORPHISMS IN THE PNMT GENE

(75) Inventors: David E. Comings, Duarte, CA (US); James P. MacMurray, Loma Linda, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/845,713

(22) Filed: May 2, 2001

(65) Prior Publication Data

US 2002/0187474 A1 Dec. 12, 2002

Related U.S. Application Data

(60) Provisional application No. 60/201,310, filed on May 2, 2000.

(51) Int. Cl.$^7$ ............................. C12Q 1/68; C07H 21/04
(52) U.S. Cl. ............................................ 435/6; 536/23.1
(58) Field of Search ............................... 536/23.1, 24.1; 435/6

(56) References Cited

PUBLICATIONS

Comings et al. Comparison of the role of dopamine, serotonin, and noradrenaline genes in ADHD, ODD and conduct disorder: multivariate regression analysis of 20 genes. Clinical Genet. 2000, vol. 57, pp. 178–196.*
Morita et al., "Organization and Complete Nucleotide Sequence of the Gene Encoding Mouse Phenylethanolamine N–Methyltransferase", Molecular Brain Research, (1992) 13:313–319.
Kaneda et al., "Molecular Cloning of cDNA and Chromosomal Assignment of the Gene for Human Phenylethanolamine N–Methyltransferase, the Enzyme for Epinephrine Biosynthesis", The Journal of Biological Chemistry Inc., (1988) 263 (16):7672–7677.
Hemmick et al., "Regulation of PNMT Gene Promoter Constructs Transfected Into the TE 671 Human Medulloblastoma Cell Line", Neuroscience Letters, (1995) 201:77–80.

Batter et al., "The Complete Nucleotide Sequence and Structure of the Gene Encoding Bovine Phenylethanolamine N–Methyltransferase", Journal of Neuroscience Research, (1988) 19:367–376.

Sawcer, S. et al., "A Genome Screen in Multiple Sclerosis Reveals Susceptibility Loci on Chromosome 6p21 and 17q22", Nature Genetics (1996) 13:464–468.

Chataway, J. et al., "A Screen of Candidates From Peaks of Linkage: Evidence for the Involvement of Myeloperoxidase in Multiple Sclerosis", Journal of Neuroimmunology, (1999) 98:208–213.

Butterfield, RJ et al., "New Genetic Loci That Control Susceptibility and Symptoms of Experimental Allergic Encephalomyelitis in Inbred Mice[1]", The Journal of Immunology, (1998) 161:1860–1867.

* cited by examiner

Primary Examiner—Anne-Marie Falk
Assistant Examiner—Celine Qian
(74) Attorney, Agent, or Firm—Rothwell, Figg, Ernst & Manbeck, p.c.

(57) ABSTRACT

The present invention is directed to two single nucleotide polymorphisms, identified as G-182A and G-387A, in the promoter region of the human phenylethanolamine N-methyltransferase (PNMT) gene, the gene products thereof, and to methods for the determination (diagnosis) of susceptibility to (risk of) neurologic or neuropsychiatric diseases involving adrenergic neurons.

6 Claims, No Drawings

POLYMORPHISMS IN THE PNMT GENE

CROSS-REFERENCE TO RELATED APPLICATION

The present application is related to U.S. provisional patent application Ser. No. 60/201,310 filed on May 2, 2000, incorporated herein by reference.

BACKGROUND OF THE INVENTION

The present invention is directed to two single nucleotide polymorphisms, identified as A/G-182 and G/A-387, in the 5' region of the human phenylethanolamine N-methyltransferase (PNMT) gene, the gene products thereof, and to methods for the determination (diagnosis) of susceptibility to (risk of) neurologic or neuropsychiatric diseases involving adrenergic neurons.

The publications and other materials used herein to illuminate the background of the invention or provide additional details respecting the practice, are incorporated by reference, and for convenience are respectively grouped in the appended Bibliography.

The noradrenergic neurons of the locus coeruleus (LC) innervate more brain areas than any other nucleus. This nucleus is involved in sleep, arousal, vigilance, attention, cognition, memory, learning, response to stress, brain activity, emotion and regulation of the autonomic nervous system (Aston-Jones et al., 1999); Aston-Jones et al., 1996). The major efferents that convey nerve impulses to the locus coeruleus derive from the epinephrine and phenylethanolamine N-methyltransferase (PNMT) rich neurons of the C1 (paragigantocellularis) and C2 (prepositus hypoglossi) nuclei of the rostral medulla oblongta (Aston-Jones, et al. (1996); Aston-Jones, et al. (1986)). These medullary centers in turn serve as the gateway between the central nervous system (CNS) and the autonomic functions of blood pressure, pulse, respiration, pain modulation, somatic sensations and skin conductance. Given this breadth of involvement, it is not surprising that defects in the noradrenergic-LC system have been implicated in a number of disorders including attention deficit disorder (Aston-Jones et al., 1999), post traumatic-stress disorder (Aston-Jones et al., 1994), depression (Siever and Davis, 1985), manic-depressive disorder (Bunney, 1977), anxiety (Aston-Jones et al., 1996), antisocial personality disorder, Alzheimer's disease (Chan-Palay, 1991) and Parkinson's disease (Chan-Palay, 1991).

The PNMT enzyme is primarily expressed in the adrenal medulla and the retina (Baetge et al., 1988). Its activity increases after stress in response to glococorticoids and neuronal stimulation (Betito et al., 1994). Since defects in epinephrine metabolism have been implicated in the etiology of attention deficit hyperactivity disorder (ADHD), aggression and anxiety (Girardi et al., 1995; Hanna et al., 1996; Klinteberg and Magnusson, 1989; Pliszka et al., 1994), PNMT is a candidate gene for a range of neurologic and neuropsychiatric disorders.

Alzheimer's Disease (AD), the most common type of dementia, is characterized by two hallmark abnormal protein deposits in the brain: beta amyloid ($\beta$A) plaques and the paired helical filaments (PHF), constituents of neurofibrillary tangles (NFT). Currently, there are three genes, and their diagnostic mutations, on chromosomes 21, 14, and 1 which have been shown to cause the early onset form of familial AD (EOAD). These three genes, the amyloid precursor protein (APP), presenilin 1 (PSEN1), and presenilin 2 (PSEN2), respectively, are responsible for the familial form of AD (FAD) where inheritance follows an autosomal-dominant fashion. Inheritance of a fourth gene, the apolipoprotein (APOE4) on chromosome 19, increases the risk of the sporadic form of late onset AD (LOAD). Additionally, loci found throughout the genome also have shown some evidence of association with the sporadic forms of LOAD (for a review see Price et al., 1998), and more recently with EOAD (Grimaldi et al., 2000). This provides strong evidence that AD is a polygenic disorder and ascribes to a multifactorial mode of inheritance in which the simultaneous action of multiple genes contributes to the disease phenotype. It is likely that not all of the genetic components of AD have been identified; therefore, further investigation is needed to elucidate additional genetic components.

Several reports have shown that selective neuronal loss in AD is a consequence of degeneration of specific neurotransmitter systems (Beal et al., 1986; Davies et al., 1980; Davies and Maloney, 1976; Perry et al., 1981; Yammamoto and Hirano, 1985), although the mechanism by which these deficits occur is for the most part unknown. One notable exception is found in a series of studies by Burke and colleagues (Burke et al., 1987) where they have shown that phenylethanolamine N-methyltransferase (PNMT) levels are decreased in the brains of persons with AD when compared to normal healthy control brains. PNMT, the rate-limiting enzyme in the catecholamine biosynthesis pathway (Axelrod et al., 1972) found on chromosome 17q21–q22 (Hoehe et al., 1992), is a specific marker for adrenergic neurons (Burke et al., 1990) because it mediates the conversion of norepinephrine (NE) to epinephrine (Epi). This suggests that PNMT is an important enzyme in the metabolism of both of these essential neurotransmitters and in AD.

Epi neurons are known to comprise approximately 85% of the C-1 neurons of the rostral ventral lateral medulla, a part of the caudal brain stem (Arango et al., 1988). Burke, et al. (1987) have demonstrated that adrenergic neurons of this region have afferent projection sites to the frontal cortex, amygdala, locus coeruleus and hippocampus. Collectively, these subcortical nuclei regulate attention, memory, emotion, and behavior. Notably, these brain regions and their associated functions are known to be affected in AD (Burke et al., 1988). Burke and colleagues found that AD patients displayed significant decreases in PNMT enzyme activity and it was determined that these decreases were due entirely to reductions in the amount of PNMT enzyme protein (Burke et al., 1988; Burke et al., 1987).

Epidemiological, twin and adoption studies have provided substantial evidence that Multiple Sclerosis (MS) has a strong genetic component (Ebers et al., 1986; Sadovnick et al., 1993; Mumford et al., 1994; Ebers et al., 1995). Research efforts have focused primarily on bi-allelic polymorphisms in candidate genes, which have been implicated in either the immune response or in myelin production (Dyment et al., 1997; Kalman and Lublin, 1999). In addition, three independent groups have performed genome screens (Ebers et al., 1996; Sawcer et al., 1996; Haines et al., 1996; Kuokkanen et al., 1997) in the hopes of elucidating novel chromosomal regions and potential candidate genes that may contribute to susceptibility to MS. Collectively, these studies provide evidence to suggest MS is a polygenic disease (Dyment et al., 1997; Bell and Lathrop, 1996), in which the additive effects of many susceptibility loci contribute to the disease phenotype.

The PNMT locus was identified in a genome screen by Swacer et al. (1996), and later by Kuokkanen, et al. (1997) to harbor a gene that may confer susceptibility to MS. In MS, the immune system mistakenly attacks self-molecules found within the brain and spinal cord (Steinman, 2000); cytokines are thought to play an intimate role in the progression of these biological effects on the CNS (Benveriste, 1995). Immune cells express various alpha-adrenergic and beta-adrenergic receptors that are sensitive to catecholamines, such as NE and EPI (Haskó and Szabó, 1998). The signaling mechanisms for the immune response are modulated by catecholaminergic input to both immune cells, which stimulate cytokine production, and adrenal cortical cells, which rely on the hypothlamo-pituitary-adrenal (HPA) stress axis to modulate glucocorticoid production (Vizi, 1998). Furthermore, modulation of immune/inflammatory mediators (like cytokines and chemokines) is dependent upon the activation of these adrenergic receptors (Haskó and Szabó, 1998) by catecholamines.

Adrenergic genes appear to play a role in bipolar disorder. Attention deficit hyperactivity disorder ADHD is a disorder of cognition and arousal (Weinberg and Harper, 1989; Mefford and Potter, 1989) and noradrenaline is closing linked to both (Aston-Jones et al., 1984; Carli et al., 1983; Usher et al., 1999). Aston-Jones et al., (2000) has correlated ADHD with tonic as opposed to phasic firing of the norepinephrine neurons in the locus coeruleus. Tonic firing in experimental animals correlates with distractability, short attention span, hyperactivity, low frustration tolerance and anxiety seen in ADHD subjects. Manic-depressive subjects in the manic phase represent an extreme state of arousal and defects in NE tone are likely to play a significant role not only in mania but also depression and the switch process (Bunney, 1977). Since the epinephrine neurons projecting from the reticular apparatus of the brain stem to the locus ceruleus, PNMT is an important candidate gene for bipolar disorders.

While the predominant theories of schizophrenia involve dopaminergic (Synder, 1976) and glutamatergic pathways, NE pathways have also been implicated (Homykiewicz, 1982). There are significant attentional, cognitive and memory defects in schizophrenia and NE pathways have been implicated in each of these areas (Arnsten and Goldman-Rakic, 1985; Arnsten et al., 1996; Sara et al., 1994). Thus, PNMT is a candidate gene for schizophrenia.

Thus, there is a continued need to identify polymorphisms of the PNMT gene as well as to discover other genes and polymorphisms involved in epinephrine metabolism, which can be used for determination (diagnosis) of susceptibility (risk) of neurologic or neuropsychiatric disorders involving adrenergic neurons, such as Alzheimer's disease, Multiple Sclerosis and other disorders and for guiding drug discovery and therapy.

SUMMARY OF THE INVENTION

The present invention is directed to two single nucleotide polymorphisms, identified as G/A-182 and G/A-387, in the 5' region of the human phenylethanolamine N-methyltransferase (PNMT) gene, the gene products thereof, and to methods for the determination (diagnosis) of susceptibility to (risk of) neurologic or neuropsychiatric diseases involving adrenergic neurons, such Alzheimer's disease (AD), Multiple Sclerosis (MS), bipolar disorder, schizophrenia and attention deficit hyperactivity disorder (AHDH).

In one aspect, the present invention is directed to a single nucleotide polymorphism in the PNMT gene responsible for the conversion of norepinephrine to epinephrine. The polymorphism, identified as G/A-182, is located in the promoter region of the PNMT gene. Position -182 is with respect to the start codon of the PNMT gene as disclosed in Baetge et al. (1988). The nucleic acid sequence of the PNMT gene is also set forth in SEQ ID NO:1. The amino acid sequence of the corresponding protein is set forth in SEQ ID NO:2.

In a second aspect, the present invention is directed to another single nucleotide polymorphism in the PNMT gene responsible for the conversion of norepinephrine to epinephrine. The polymorphism, identified as G/A-387, is located in the promoter region of the PNMT gene. Position -387 is with respect to the start codon of the PNMT gene as disclosed in Baetge et al. (1988).

In a third aspect, the present invention is directed to a novel method of using genotyping for the polymorphisms to allow individuals to be divided into groups at risk for neurologic or neuropsychiatric diseases involving adrenergic neurons by determining the presence of the G-182, A-182, G-387 and A-387 alleles of the PNMT gene. In one embodiment, the method involves genotyping for the polymorphisms to allow individuals to be divided into groups at risk for Alzheimer's disease based on the degree of linkage disequilibrium and determining the presence of the G-182, A-182, G-387 and A-387 alleles of the PNMT gene, wherein doubly heterozygous individuals are at the lowest risk for Alzheimer's disease and doubly homozygous individuals are at the highest risk for Alzheimer's disease. In a second embodiment, the method allows genotyping for the polymorphisms to allow individuals to be divided into groups at risk for Multiple Sclerosis (MS), wherein the G/G-387 homozygote is associated with MS, especially in combination with the A/A-182 and the A/G-182 alleles. In a third embodiment, the method allows genotyping for the polymorphisms to allow individuals to be divided into groups at risk for bipolar disorder, wherein the presence of double heterozygosity is associated with manic depressive behavior. In a fourth embodiment, the method allows genotyping for the polymorphisms to allow individuals to be divided into groups at risk for attention deficit hyperactivity disorder (ADHD), wherein the presence of double heterozygosity is associated with ADHD. In a fifth embodiment, the method allows genotyping for the polymorphisms to allow individuals to be divided into groups at risk for schizophrenia, wherein a decrease in heterozygosity is associated with schizophrenia. These polymorphisms can be analyzed individually or as part of a panel of polymorhphisms which have been associated with these disorders.

In a fourth aspect, the present invention is directed to a method of using the genotype of the above identified polymorphisms as a predictor of neurologic or neuropsychiatric diseases involving adrenergic neurons or a risk for neurologic or neuropsychiatric diseases involving adrenergic neurons.

In a fifth aspect of the invention, analysis of the PNMT gene is further provided for diagnosis of subjects with neurologic or neuropsychiatric diseases involving adrenergic neurons or as a genetic test of risk for neurologic or neuropsychiatric diseases involving adrenergic neurons. The diagnostic method comprises analyzing the DNA sequence of the PNMT gene of an individual to be tested and comparing it with the DNA sequence of the native, non-variant genes. In a second embodiment, the PNMT gene of an individual to be tested is screened for polymorphisms associated with neurologic or neuropsychiatric diseases involving adrenergic neurons. The ability to predict neurologic or neuropsychiatric diseases involving adrenergic neurons will enable physicians to treat this disease with appropriate medical therapies.

In a sixth aspect of the present invention, the polymorphisms in the PNMT gene are used for drug screening and testing.

DETAILED DESCRIPTION OF THE INVENTION

The present invention is directed to two single nucleotide polymorphisms in the promoter region of the human phenylethanolamine N-methyltransferase PNMT gene, the gene products thereof, and to methods for the determination (diagnosis) of susceptibility to (risk of) neurologic or neuropsychiatric diseases involving adrenergic neurons.

Two Southern blot polymorphisms of the PNMT gene (Ban I and HgiA I) have been reported by Hoehe et al. (1989a; 1989b), but the site and type of the nucleic acid substitution was not reported. To aid in the investigation of the role of the PNMT gene in psychiatric and other disorders, we identified two SNPs: A/G-182 and G/A-387 in the 5' region of the PNMT gene responsible for the conversion of norepinephrine to epinephrine. These SNPs are numbered with respect to the start site of transcription of the wildtype sequence set forth in SEQ ID NO:1. The start site of transcription is nucleotide 1935 in SEQ ID NO:1. Hence the positions of the two SNPs in SEQ ID NO:1 are 1571 and 1776 for the -387 and -182 polymorphisms, respectively. These polymorphisms have also been referred to as -353 and -148 in Wu and Comings (1999).

The present invention provides methods of screening the PNMT gene to identify polymorphisms, particularly polymorphisms strongly associated with neurologic or neuropsychiatric diseases involving adrenergic neurons. Examples of such diseases include, but are not limited to, Alzheimer's disease (AD), Multiple Sclerosis (MS), bipolar disorder, schizophrenia and attention deficit hyperactivity disorder (ADHD). Such methods may further comprise the step of amplifying a portion of the gene, and may further include a step of providing a set of polynucleotides which are primers for amplification of said portion of the gene. The methods are useful for identifying polymorphisms for use in diagnosis and treatment of such neurologic or neuropsychiatric diseases.

The present invention provides the information necessary for physicians to select drugs for use in the treatment of such neurologic or neuropsychiatric diseases. With the discovery of the association of mutations in the PNMT gene and neurologic or neuropsychiatric diseases involving adrenergic neurons, drugs which are known PNMT inhibitors can be selected for the treatment of such diseases and other disorders.

The present invention also provides a method for screening drug candidates to identify drugs useful for treating neurologic or neuropsychiatric diseases involving adrenergic neurons. Drug screening is performed by comparing the activity of native genes and those described herein in the presence and absence of potential drugs.

The present invention further provides methods for genotyping individuals at risk for neurologic or neuropsychiatric diseases involving adrenergic neurons. Such methods analyze the PNMT gene for the polymorphisms described herein. The genotyping is particularly useful for testing potential drugs for effects on neurologic or neuropsychiatric diseases involving adrenergic neurons. The genotyping can also include the identification of other disorders that will respond to drugs that inhibit PNMT activity.

Proof that the PNMT gene is associated with neurologic or neuropsychiatric diseases involving adrenergic neurons or with a risk for such diseases is obtained by finding polymorphisms or sequences in DNA extracted from affected individuals which create abnormal PNMT gene products or abnormal levels of the gene products or which are statistically associated with such diseases. Such susceptibility alleles will be present at a much higher frequency in individuals who have such diseases than in individuals who do not. The examples which are set forth herein show such an association for Alzheimer's disease, Multiple Sclerosis, bipolar disorders (such as manic depressive and ADHD) and schizophrenia.

According to the diagnostic and prognostic method of the present invention, the genotype of an individual with respect to the polymorphisms at -182 and -387 of the PNMT gene is determined. Any technique which is capable of identifying the genotype of the individual at these positions may be used. Thus, useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful are the recently developed techniques of mass spectroscopy (such as MALDI or MALDI-TOF; Fu et al. 1998), DNA microchip technology and fluorescent flow cytometric analysis (Taylor et al., 2001).

The presence of neurologic or neuropsychiatric diseases involving adrenergic neurons or risk for neurologic or neuropsychiatric diseases involving adrenergic neurons may be ascertained by testing any tissue of a human for the -182 and -387 polymorphisms PNMT gene. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for the -182 and -387 polymorphisms of the PNMT gene.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele-specific detection approach such as allele-specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of individuals having neurologic or neuropsychiatric diseases or disorders. Southern blots displaying hybridizing fragments (differing in length from control DNA when probed with sequences near or including the PNMT locus) indicate a possible mutation. If restriction enzymes which produce very large restriction fragments are used, then pulsed field gel electrophoresis (PFGE) is employed. Alternatively, the desired region of the PNMT locus can be amplified, the resulting amplified products can be cut with a restriction enzyme and the size of fragments produced for the different polymorphisms can be determined.

Detection of point mutations may be accomplished by molecular cloning of the PNMT alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single-stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); 6) allele-specific PCR (Ruano and Kidd, 1989); and 7) PCR amplification of the site of the polymorphism followed by digestion using a restriction endonuclease that cuts or fails to cut when the variant allele is present. For allele-specific PCR, primers are used which hybridize at their 3' ends to a particular PNMT polymorphism or mutation. If the particular polymorphism or mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type PNMT gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the PNMT gene can also be detected using Southern blot hybridization, especially if the changes are gross rearrangements, such as deletions and insertions.

DNA sequences of the PNMT gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified PNMT sequences can be performed, for example, on a nylon filter. Hybridization to a particular probe under high stringency hybridization conditions indicates the presence of the same mutation in the tissue as in the allele-specific probe.

Once the site containing the polymorphisms has been amplified, the SNP (single nucleotide polymorphism) can also be detected by primer extension. Here a primer is annealed immediately adjacent to the variant site, and the 5' end is extended a single base pair by incubation with di-deoxytrinucleotides. Whether the extended base was a A, T, G or C can then be determined by mass spectrometry (MALDI-TOF) (Fei et al, 1998) or fluroescent flow cytometric analysis (Taylor et al, 2001) or other techniques.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen individuals for mutations in the breast cancer gene BRCA1 (Hacia et al., 1996). This new technology has been reviewed in a news article in *Chemical and Engineering News* (Borman, 1996) and been the subject of an editorial (Editorial, Nature Genetics, 1996). Also see Fodor (1997).

The most definitive test for mutations in a candidate locus is to directly compare genomic PNMT sequences from patients with those from a control population. Alternatively, one could sequence messenger RNA after amplification, e.g., by PCR, thereby eliminating the necessity of determining the exon structure of the candidate gene.

Mutations falling outside the coding region of PNMT can be detected by examining the non-coding regions, such as introns and regulatory sequences near or within the genes. An early indication that mutations in non-coding regions are important may come from Northern blot experiments that reveal messenger RNA molecules of abnormal size or abundance in patients as compared to those of control individuals.

Alteration of PNMT mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type protein. For example, monoclonal antibodies immunoreactive with PNMT can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered protein can be used to detect alteration of the wild-type PNMT gene. Functional assays, such as protein binding determinations, can be used. In addition, assays can be used which detect PNMT biochemical function. Finding a mutant PNMT gene product indicates alteration of a wild-type PNMT gene.

A mutant PNMT gene or corresponding gene products can also be detected in other human body samples which contain DNA, such as serum, stool, urine and sputum. The same techniques discussed above for detection of mutant genes or gene products in tissues can be applied to other body samples. By screening such body samples, a simple early diagnosis can be achieved for subjects at risk for Alzheimer's disease.

The primer pairs of the present invention are useful for determination of the nucleotide sequence of a particular PNMT allele using PCR. The pairs of single-stranded DNA primers can be annealed to sequences within or surrounding the gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular PNMT polymorphic or mutant alleles, and thus will only amplify a product in the presence of the polymorphic or mutant allele as a template.

In order to facilitate subsequent cloning of amplified sequences, primers may have restriction enzyme site sequences appended to their 5' ends. Thus, all nucleotides of the primers are derived from the gene sequence or sequences adjacent the gene, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of each gene and polymorphisms described herein, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern blot hybridization to genomic DNA and in the RNase protection method for detecting point mutations already discussed above. The probes can be used to detect PCR amplification products. They may also be used to detect mismatches with the PNMT gene or mRNA using other techniques.

The presence of an altered (or a mutant) PNMT gene has been associated with Alzheimer's disease or risk of Alzheimer's disease. In order to detect a PNMT gene polymorphism or mutation, a biological sample is prepared and analyzed for a difference between the sequence of the allele being analyzed and the sequence of the wild-type allele. Polymorphic or mutant alleles can be initially identified by any of the techniques described above. The polymorphic or mutant alleles are then sequenced to identify the specific polymorphism or mutation of the particular allele. Alternatively, polymorphic or mutant alleles can be initially identified by identifying polymorphic or mutant (altered) proteins, using conventional techniques. The alleles are then sequenced to identify the specific polymorphism or mutation for each allele. The polymorphisms or mutations, especially those statistically associated with Alzheimer's disease, are then used for the diagnostic and prognostic methods of the present invention.

Definitions

The present invention employs the following definitions, which are, where appropriate, referenced to PNMT.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the PNMT region are preferably complementary to, and hybridize specifically to, sequences in the PNMT region or in regions that flank a target region therein. PNMT sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the PNMT polypeptide and fragments thereof or to polynucleotide sequences from the PNMT region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the PNMT polypeptide or fragment. Monoclonal antibodies may be made by injecting mice with the protein polypeptides, fusion proteins or fragments thereof. Monoclonal antibodies will be screened by ELISA and tested for specific immunoreactivity with PNMT polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is in the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-9}$ M$^{-1}$ or preferably $10^{-9}$ to $10^{-10}$ M$^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"PNMT Allele" refers, respectively, to normal and variant alleles of the PNMT locus.

"PNMT Locus", "PNMT Gene", "PNMT Nucleic Acids" or "PNMT Polynucleotide" each refer to polynucleotides, all of which are in the PNMT region, respectively, that are likely to be expressed in normal tissue, certain alleles of which are associated with Alzheimer's disease or risk of Alzheimer's disease. The PNMT locus is intended to include coding sequences, intervening sequences and regulatory elements controlling transcription and/or translation. The PNMT locus is intended to include all allelic variations of the DNA sequence.

These terms, when applied to a nucleic acid, refer to a nucleic acid which encodes a human PNMT polypeptide, fragment, homolog or variant, including, e.g., protein fusions or deletions. The nucleic acids of the present invention will possess a sequence which is either derived from, or substantially similar to a natural PNMT-encoding gene or one having substantial homology with a natural PNMT-encoding gene or a portion thereof.

The PNMT gene or nucleic acid includes normal alleles of the PNMT gene, respectively, including silent alleles having no effect on the amino acid sequence of the PNMT polypeptide as well as alleles leading to amino acid sequence variants of the PNMT polypeptide that do not substantially affect its function. These terms also include alleles having one or more mutations which adversely affect the function of the PNMT polypeptide. A mutation may be a change in the PNMT nucleic acid sequence which produces a deleterious change in the amino acid sequence of the PNMT polypeptide, resulting in partial or complete loss of PNMT function, respectively, or may be a change in the nucleic acid sequence which results in the loss of effective PNMT expression or the production of aberrant forms of the PNMT polypeptide.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally-occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the PNMT region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a PNMT-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Manrheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the PNMT locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides.

"PNMT protein" or "PNMT polypeptide" refers to a protein or polypeptide encoded by the PNMT locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native PNMT sequence, preferably in excess of about 90%, and more preferably at least about 95% homologous. Also included are proteins encoded by DNA which hybridize under high or low stringency conditions, to PNMT-encoding nucleic acids and closely related polypeptides or proteins retrieved by antisera to the PNMT protein (s).

The PNMT polypeptide may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the PNMT polypeptide. Such polypeptides may have an amino acid sequence which differs from the wild-type by one or more of addition, substitution, deletion or insertion of one or more amino acids.

"Operably linked" refers to a juxtaposition wherein the components so described are in a relationship permitting them to function in their intended manner. For instance, a promoter is operably linked to a coding sequence if the promoter affects its transcription or expression.

The terms "peptide mimetic" or "mimetic" are intended to refer to a substance which has the essential biological activity of the PNMT polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural PNMT polypeptide.

"Probes". Polynucleotide polymorphisms associated with PNMT alleles which are associated with an inability to overcome nicotine addition are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out non-specific/ adventitious bindings, that is, which minimize noise. (It should be noted that, throughout this disclosure, if it is stated simply that "stringent" conditions are used, that it is meant to be read that "high stringency" conditions are used.) Since such indications identify neutral DNA polymorphisms as well as mutations, these indications need further analysis to demonstrate detection of a PNMT susceptibility allele.

Probes for PNMT alleles may be derived from the sequences of the PNMT region, its cDNA, functionally equivalent sequences, or the complements thereof. The probes may be of any suitable length, which span all or a portion of the PNMT region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding PNMT are preferred as probes. This definition therefore includes probes of sizes 8 nucleotides through 6000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30,38, 50, 72, 121, etc., nucleotides), or probes having more than 500 nucleotides. The probes may also be used to determine whether mRNA encoding PNMT is present in a cell or tissue. The present invention includes all novel probes having at least 8 nucleotides, its complement or functionally equivalent nucleic acid sequences. The present invention does not include probes which exist in the prior art.

Similar considerations and nucleotide lengths are also applicable to primers which may be used for the amplification of all or part of the PNMT gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 6000. The primers may also be used to determine whether mRNA encoding PNMT is present in a cell or tissue. The present invention includes all novel primers having at least 8 nucleotides derived from the PNMT locus for amplifying the PNMT gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for PNMT polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of PNMT polypeptides. Immunological activities include both immunogenic function in a target immune system, as well as sharing of immunological epitopes for binding, serving as either a competitor or substitute antigen for an epitope of the PNMT protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for PNMT polypeptides or fragments thereof is described below.

The present invention also provides for fusion polypeptides, comprising PNMT polypeptides and fragments. Homologous polypeptides may be fusions between two or more PNMT polypeptide sequences or between the sequences of PNMT and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the PNMT polypeptides from other biological material, such as from cells transformed with recombinant nucleic acids encoding PNMT, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A PNMT protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in Guide to Huge Computers, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Asubel, 1992; Wetmur and Davidson, 1968.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42 C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65 C.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type PNMT nucleic acid or wild-type PNMT polypeptide. The modified polypeptide will be substantially homologous to the wild-type PNMT polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type PNMT polypeptide. Alternatively, the similarity of function (activity) of the modified polypeptide may be higher than the activity of the wild-type PNMT polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type PNMT gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Recombinant or chemically synthesized nucleic acids or vectors, transformation or transfection of host cells, transformed or transfected host cells and polypeptides are produced using conventional techniques, such as described in U.S. Pat. Nos. 5,837,492; 5,800,998 and 5,891,628, each incorporated herein by reference.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art, including those described in U.S. Pat. Nos. 5,837, 492; 5,800,998 and 5,891,628, each incorporated herein by reference.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing are generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to, or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an PNMT specific binding partner, or to find mimetics of the PNMT polypeptide.

Following identification of a substance which modulates or affects polypeptide activity, the substance may be further investigated. Furthermore, it may be manufactured and/or used in preparation, i.e., a manufacture or formulation, or a composition such as a medicament, pharmaceutical composition or drug. These may be administered to individuals.

In order to detect the presence of a PNMT allele predisposing an individual to an inability to overcome nicotine addition, a biological sample such as blood is prepared and analyzed for the presence or absence of susceptibility alleles of PNMT. In order to detect the presence of an inability to overcome nicotine addition or as a prognostic indicator, a biological sample is prepared and analyzed for the presence or absence of polymorphic or mutant alleles of PNMT. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis. Suitable diagnostic techniques include those described herein as well as those described in U.S. Pat. Nos. 5,837,492; 5,800,998 and 5,891, 628, each incorporated herein by reference.

Initially, the screening method involves amplification of the relevant PNMT sequence. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of PNMT. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection of the resulting hybrid, if any, is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding PNMT. Allele-specific probes are also contemplated within the scope of this example, and exemplary allele-specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

The presence of an inability to overcome nicotine addition can also be detected on the basis of the alteration of wild-type PNMT polypeptide. Such alterations can be determined by sequence analysis in accordance with conventional techniques. More preferably, antibodies (polyclonal or monoclonal) are used to detect differences in, or the absence of PNMT peptides. Techniques for raising and purifying antibodies are well known in the art, and any such techniques may be chosen to achieve the preparations claimed in this invention. In a preferred embodiment of the invention, antibodies will immunoprecipitate PNMT proteins from solution as well as react with these proteins on Western or immunoblots of polyacrylamide gels. In another preferred embodiment, antibodies will detect PNMT proteins in paraffin or frozen tissue sections, using immunocytochemical techniques.

Preferred embodiments relating to methods for detecting PNMT or its polymorphisms/mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

According to the present invention, a method is also provided of supplying wild-type PNMT function to a cell which carries a mutant PNMT allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner. Conventional methods are employed, including those described in U.S. Pat. Nos. 5,837,492; 5,800,998 and 5,891,628, each incorporated herein by reference.

Alternatively, peptides which have PNMT activity can be supplied to cells which carry a mutant or missing PNMT allele. Protein can be produced by expression of the cDNA sequence in bacteria, for example, using known expression vectors. Alternatively, the polypeptide(s) can be extracted from polypeptide-producing mammalian cells. In addition, the techniques of synthetic chemistry can be employed to synthesize the protein. Any of such techniques can provide the preparation of the present invention which comprises the PNMT protein. The preparation is substantially free of other human proteins. This is most readily accomplished by synthesis in a microorganism or in vitro. Active PNMT molecules can be introduced into cells by microinjection or by use of liposomes, for example. Alternatively, some active molecules may be taken up by cells, actively or by diffusion. Conventional methods are employed, including those described in U.S. Pat. Nos. 5,837,492; 5,800,998 and 5,891,628, each incorporated herein by reference.

Animals for testing therapeutic agents or for developing animal and cellular models can be selected after mutagenesis of whole animals or after treatment of germline cells or zygotes. Such treatments include insertion of polymorphic/mutant PNMT alleles, usually from a second animal species, as well as insertion of disrupted homologous genes. Alternatively, the endogenous PNMT gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). These transgenic, transplacement and knock-out animals can also be used to screen drugs that may influence the biochemical, neuropathological, and behavioral parameters relevant to an inability to overcome nicotine addition. Cell lines can also be derived from these animals for use as cellular models, or in drug screening. Conventional methods are employed, including those described in U.S. Pat. Nos. 5,837,492; 5,800,998 and 5,891,628, each incorporated herein by reference.

The identification of the association between the PNMT gene polymorphism/mutations and Alzheimer's disease permits the early presymptomatic screening of individuals to identify those at risk for developing Alzheimer's disease or to identify the cause of such disorders. To identify such individuals, the alleles are screened as described herein or using conventional techniques, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele-specific oligonucleotide (ASO), dot blot analysis and PCR-SSCP analysis. Also useful is the recently developed technique of DNA microchip technology. Such techniques are described in U.S. Pat. Nos. 5,837,492; 5,800,998 and 5,891,628, each incorporated herein by reference.

Genetic testing will enable practitioners to identify individuals at risk for nicotine addition or an inability to overcome nicotine addition at, or even before, birth. Presymptomatic diagnosis will enable better treatment of these disorders, including the use of existing medical therapies. Genetic testing will also enable practitioners to identify individuals having diagnosed disorders those in which the diagnosis results from PNMT. Genotyping of such individuals will be useful for (a) identifying subtypes of depression that will respond to drugs that inhibit PNMT activity, (b) identifying subtypes of depression that respond well to placebos versus those that respond better to active drugs and (c) guide new drug discovery and testing. This genotyping is particularly useful, since 30% to 50% of antidepressant drug response results from a placebo response which may be caused by the present genes.

The PNMT polypeptides, antibodies, peptides and nucleic acids of the present invention can be formulated in pharmaceutical compositions, which are prepared according to conventional pharmaceutical compounding techniques. See, for example, *Remington's Pharmaceutical Sciences,* 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. Nos. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be-implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936. Standard techniques well known in the art or the techniques specifically described herein are utilized.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); Riott, *Essential Immunology,* 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Identification of Polymorphisms in the PNMT Gene

Based on the 5' flanking sequences published from +1 to –1923 (Baetge et al., 1988), we screened this region of the PNMT gene by SSCP analysis (Podulso et al., 1991) followed by direct sequencing of PCR products. The two sets of primers used are shown in Table 1.

TABLE 1

PCR Primers for the G-182A and G-387A Polymorphisms of the PNMT gene

| Variant | Primer Sequence (SEQ ID NO:) | PCR product (bp) | Restriction enzyme | Annealing temperature |
|---------|------------------------------|------------------|--------------------|-----------------------|
| G-182A  | 5'CGGGACAAGTACGGAGCC3' (3)   | 101 bp           | Msp I              | 60° C.                |
|         | 5'CCATCTCCCTTAGTGTCC3' (4)   |                  |                    |                       |
| G-387A  | 5'GTCTCCACCTCGAATCAG3' (5)   | 86 bp            | Mnl I              | 58° C.                |
|         | 5'CCATCTCTCTTCTCCAGC3' (6)   |                  |                    |                       |

Standard PCR was carried out in a 15 µl volume containing 50 ng genomic DNA, 200 nM of each primer, 200 µM dNTPs, and 0.6U Taq DNA polymerase (QIAGEN, Santa Clarita, Calif.). The amplification was performed for 35 cycles with denaturation at 95° C. for 40 sec, annealing temperature 60° C. for G-182A or 58° C. for G-387A for 40 sec and elongation at 72° C. for 40 sec. The amplified products were digested with Msp I for G-182A or Mnl I (New England Biolabs, Beverly, Mass.) for G-387A, and the resulting polymorphic fragments were separated on a 10% polyacrylamide gel in 1×TBE buffer, respectively. Then they were stained with ethidium bromide (5 µg/ml). Cleavage of the 86 bp G-387A PCR product with Mnl I identifies the G allele, 44 bp, and the A allele, 27 bp+17 bp. There are two G-387A constant bands, which are 24 bp+18 bp in length. Cleavage of the 101 bp G-182A PCR product with Msp I identifies the A allele, 65 bp, and the G allele, 49 bp+16 bp. There are two G-182A constant bands, which are 19 bp+17 bp in length.

We found that the two polymorphisms are in partial linkage disequilibrium, and genotyping for both polymorphisms allowed individuals to be divided into four groups based on the degree of linkage disequilibrium. The frequency of alleles on the two SNPs was determined in 164 unrelated Caucasian controls without psychiatric disorders. The heterozygosity index of SNP G-182A was 0.43 with the frequency of allele G being 0.42 and allele A 0.58, and SNP G-387A was 0.35 with the frequency of allele G being 0.39 and allele A 0.61. The G-182 and A-387 alleles are in strong linkage disequilibrium. A cross tabulation of genotypes of 688 controls and subjects genotyped at both polymorphisms showed that 71 percent matched for G-182/G-182 with A-387/A-387, heterozygotes with heterozygotes, and A-182/A-182 with G-387/G-387. The frequency of the groups was compared in controls, subjects with early onset Alzheimer's disease (EOA), and subjects with late onset Alzheimer's disease (LOA). There was a highly significant increase in the frequency of groups showing linkage disequilibrium and decrease in the frequency of the group showing maximum linkage disequilibrium for controls verses those with EOA, and to a lesser extent those with LOA (p<0.00000001).

Example 2

Analysis of PNMT Polymorphisms and Alzheimer's Disease

AD Subjects: All subjects examined in this study were non-Hispanic Caucasians. DNA was isolated from 131 brain samples, 39 EOAD and 92 LOAD patients, with a postmortem confirmed diagnosis of AD from the Human Neurological Research Specimen Bank at Los Angeles Veterans Affairs Medical Center, Los Angeles, Calif. Patients were grouped according to age at onset. Those with an age of onset of 65 years of age or less were termed Early Onset Alzheimer's Disease or EOAD. Those with an age of onset of 65 years of age or greater were termed Late Onset Alzheimer's Disease or LOAD. These age distinctions were based on studies of others (Terry and Davies, 1980; Terry and Katzman, 1983; Kehoe et al., 1999). The distribution of the age at death for the EOAD cases had a range of 55–78 years, with a mean age of 65.6 years. The age at onset of EOAD cases ranged between 49 and 64 years, with a mean onset age of 58.5 years. The distribution of the age at death for the LOAD cases ranged from 67–97 years, with a mean age of 80.8 years. The age at onset of the LOAD cases range of 65–94, with a mean onset age of 75.3.

Control Subjects: DNA was obtained from blood leukocytes for control samples (n=940) which consisted of four cohorts: (1) 171 adult students from a nearby university; (2) 575 parents of twins from the Minnesota Twin and Family Study; (3) 124 adult patients from Loma Linda University; and (4) 77 adult patients from a local Veterans hospital. The patients in the latter two groups had non-dementing medical conditions. The age range of those control subjects was 23–74, with a mean of 43.7 years. This control group was partitioned into two groups based on age. Group I consisted of 824 controls ranging from 23 to 54, with a mean of 41.2 years. Group II consisted of 116 controls ranging in age from 55 to 74, with a mean of 61.0 years. All studies were approved by the IRB committees of the involved institutions and each subject signed a consent form.

Genetic Methods: Two polymorphic loci in the promoter region of the PNMT gene were studied (Wu and Comings, 2000). Both of the polymorphisms consist of a G to A transition, at one position -387, and the other at -182 with respect to the gene transcription start site. Two regions of the promoter corresponding to the polymorphic loci were amplified by a PCR kit (Quiagen, Santa Clarita, CA) and the primer sets for -387 and -182 as shown in Table 1. The PCR reaction was performed using standard procedures in a 15 ml volume containing 50 ng of genomic DNA, 200 nM of each primer, 200 uM dNTP's, and 0.6 U of DNA Taq polymerase and buffer supplied by the manufacturer. Amplification for each of the markers was performed for 35 cycles with denaturation at 95° C. for 40s, annealing temp of 60° C. for G-182A or 58° C. for G-387A for 40s and elongation at 72° C. for 40s.

The amplified products were digested by Mnl I and Msp I restriction enzymes, for G-387A and G-182A respectively, and the resulting restriction fragments were separated on a 10% polyacrylamide gel in 1×TBE buffer and visualized by staining with 5 µg of ethidium bromide. Cleavage of the 86 bp G-387A PCR product with Mnl I identifies the G allele, 44 bp, and the A allele, 27 bp+17 bp. There are two G-387A constant bands, which are 24 bp+18 bp in length. Cleavage of the 101 bp G-182A PCR product with Msp I identifies the A allele, 65 bp, and the G allele, 49 bp+16 bp. There are two G-182A constant bands, which are 19 bp+17 bp in length.

Statistical Methods: Alleles and genotypes were counted and their distributions between groups were determined. The Chi-square ($\chi^2$) test was employed to statistically compare these groups. When appropriate, a Bonferroni correction for multiple comparisons were made. Differences were considered significant at (p≧0.05). Linkage disequilibrium was tested as described by Lynch and Walsh (1998). All statistical data calculations were done with the SPSS statistical package for Macintosh (release 6.1.1) (SPSS, Inc, Chicago, Ill.).

Results: The distribution of the two PNMT promoter polymorphisms was analyzed in AD patients and controls. The genotypic distributions of these markers, at positions G-387A and G-182A, are shown in Table 2. The four control groups were examined for possible differences in allele frequencies and genotype prevalence. No significant differences were observed between the four control groups. However, statistically significant results were observed in EOAD when compared to all of the control groups for both the G-387A ($X^2$=7.56; p=0.023) and G-182A ($\chi^2$=8.91; p=0.012) PNMT markers. In EOAD, both markers showed the strongest statistical association when compared to the Group II controls, -387 ($X^2$=7.57; p=0.023) and -182 ($\chi^2$=11.45; p=0.003). In contrast, LOAD demonstrated no statistically significant association with either the G-387A (all controls: $\chi^2$=4.03; p=0.133; Group I controls: $\chi^2$=4.17; p=0.125; Group II controls: $\chi^2$=2.23; p=0.328) or G-182A (all controls: $\chi^2$=0.19; p=0.91; Group I controls: $\chi^2$=0.31; p=0.856; Group II controls: $\chi^2$=2.36; p=0.307) markers when compared to any of the control groups.

TABLE 2

Patients with Alzheimer's Disease (AD) and Controls with the PNMT G (-387)/A (-387) and G (-182)/A (-182) Genotypes.

| PNMT | Genotype(-387) No. of Patients | | | | | Genotype(-182) No. of Patients | | | | |
|---|---|---|---|---|---|---|---|---|---|---|
| | GG | G/A | AA | $\chi^2$ | p | GG | G/A | AA | $\chi^2$ | p |
| AD Subjects (n = 131) | 34 | 40 | 57 | 8.31 | 0.0157 | 32 | 50 | 49 | 3.31 | 0.1911 |
| EOAD Subjects (n = 39) | 10 | 8 | 21 | 7.56 | 0.0229 | 13 | 9 | 17 | 8.91 | 0.0116 |
| LOAD Subjects (n = 92) | 24 | 32 | 36 | 4.03 | 0.1332 | 19 | 41 | 32 | 0.19 | 0.9096 |
| All Control Subjects (n = 947) | 172 | 404 | 371 | | | 178 | 430 | 339 | | |

TABLE 2-continued

Patients with Alzheimer's Disease (AD) and Controls
with the PNMT G (−387)/A (−387) and G (−182)/A (−182) Genotypes.

| PNMT | Genotype(−387) No. of Patients | | | | | Genotype(−182) No. of Patients | | | | |
|---|---|---|---|---|---|---|---|---|---|---|
| | GG | G/A | AA | $\chi^2$ | p | GG | G/A | AA | $\chi^2$ | p |
| AD Subjects (n = 131) | 34 | 40 | 57 | 8.19 | 0.0167 | 32 | 50 | 49 | 2.82 | 0.2445 |
| EOAD Subjects (n = 39) | 10 | 8 | 21 | 7.36 | 0.0253 | 13 | 9 | 17 | 8.33 | 0.0156 |
| LOAD Subjects (n = 92) | 24 | 32 | 36 | 4.17 | 0.1246 | 19 | 41 | 32 | 0.31 | 0.8561 |
| Group I Control Subjects (n = 824) | 147 | 349 | 328 | | | 154 | 363 | 307 | | |
| AD Subjects (n = 131) | 34 | 40 | 57 | 5.38 | 0.0679 | 32 | 50 | 49 | 6.65 | 0.036 |
| EOAD Subjects (n = 39) | 10 | 8 | 21 | 7.57 | 0.0228 | 13 | 9 | 17 | 11.45 | 0.0033 |
| LOAD Subjects (n = 92) | 24 | 32 | 36 | 2.23 | 0.3275 | 19 | 41 | 32 | 2.36 | 0.307 |
| Group II Control Subjects (n = 116) | 24 | 52 | 40 | | | 23 | 63 | 30 | | |

All AD subjects (EOAD and LOAD) showed significant association for the G-387A marker when compared to both the total controls ($\chi^2$=8.31; p=0.016) and Group I controls ($\chi^2$=8.19; p=0.017. Similarly, significant association was observed for the G-182A marker with total AD subjects when compared to the Group II control subjects ($\chi^2$=6.65; p=0.036), but not when compared to either total controls ($\chi^2$=3.31; p=0.191) or Group I controls ($\chi^2$=2.82; p=0.245)

Linkage disequilibrium testing was performed using both PNMT markers. The G-387A and G-182A PNMT promoter SNPs were not in linkage disequilibrium (D=−0.176; Std. Error=0.008). This suggests that the markers were contributing differently to AD, which prompted evaluation of the two markers for interactions that might reveal an additive effect on the AD phenotype.

Genotype distributions of the PNMT (G-387A/G-182A) markers are shown in Table 3. Statistically significant differences were observed for EOAD when compared to the total control group ($\chi^2$=25.3; p=0.00272), control Group I ($\chi^2$=25.95; p=0.00214), and control Group II ($\chi^2$=21.03; p=0.01408). In EOAD patients, the data for both the G-387A and G-182A PNMT markers from Table 2 show that strong molecular heterosis (Comings and MacMurray, 2000) exists, where the heterozygous genotype is under-represented when compared to either homozygous genotype. Similarly, from Table 3, one of the striking differences seen in Table 3 is the substantial reduction of the double heterozygous (GA/AG) genotype. This genotype was present in only 2.6% of all EOAD patients, whereas in control subjects this genotype was present in 31.7 to 37.9% of the subjects. The heterozygous conditions for both markers are severely under-represented in EOAD patients. These findings suggest that the HET/HET (GA/AG) genotype combination appears to act in a protective fashion for EOAD susceptibility. Support for this is shown by the fact that every other G-387A/G-182A genotype combination shows increases in EOAD when compared to all control groups. In total controls, two main genotypic combinations (GA/AG and the AA/AA), account for 61.5% of all genotypes, whereas in EOAD, the same two genotypic combinations (GA/AG and AA/AA) represent only 32.4% of all genotypic combinations.

TABLE 3

Distribution of the PNMT −387/−182
Polymorphisms in Patients with AD and Controls

| PNMT (−387/−182) | ALL AD | EOAD | LOAD | Total Controls |
|---|---|---|---|---|
| GG/AA | 3 (2.3) | 1 (2.6) | 2 (2.2) | 14 (1.5) |
| GG/AG | 13 (9.9) | 2 (5.1) | 11 (12.0) | 39 (4.1) |
| GG/GG | 18 (13.7) | 7 (17.9) | 11 (12.0) | 119 (12.6) |
| GA/AA | 8 (6.1) | 4 (10.3) | 4 (4.3) | 50 (5.3) |
| GA/AG | 24 (18.3) | 1 (2.6) | 23 (25.0) | 308 (32.5) |
| GA/GG | 8 (6.1) | 3 (7.7) | 5 (5.4) | 46 (4.9) |
| AA/AA | 38 (29.0) | 12 (30.8) | 26 (28.3) | 275 (29.0) |
| AA/AG | 13 (9.9) | 6 (15.4) | 7 (7.6) | 83 (8.8) |
| AA/GG | 6 (4.6) | 3 (7.7) | 3 (3.3) | 13 (1.4) |
| n | 131 | 39 | 92 | 947 |
| Mean Age | 76.2 | 65.6 | 80.8 | 43.7 |
| | $\chi^2$ = 23.57971 | $\chi^2$ = 25.33513 | $\chi^2$ = 14.76896 | |
| | DF = 8 | DF = 8 | DF = 8 | |
| | p = 0.00269 | p = 0.00136 | p = 0.06380 | |

| PNMT (−387/−182) | ALL AD | EOAD | LOAD | Group I Controls |
|---|---|---|---|---|
| GG/AA | 3 (2.3) | 1 (2.6) | 2 (2.2) | 13 (1.6) |
| GG/AG | 13 (9.9) | 2 (5.1) | 11 (12.0) | 32 (3.9) |
| GG/GG | 18 (13.7) | 7 (17.9) | 11 (12.0) | 102 (12.4) |
| GA/AA | 8 (6.1) | 4 (10.3) | 4 (4.3) | 46 (5.6) |
| GA/AG | 24 (18.3) | 1 (2.6) | 23 (25.0) | 261 (31.7) |
| GA/GG | 8 (6.1) | 3 (7.7) | 5 (5.4) | 42 (5.1) |
| AA/AA | 38 (29.0) | 12 (30.8) | 26 (28.3) | 248 (30.1) |
| AA/AG | 13 (9.9) | 6 (15.4) | 7 (7.6) | 70 (8.5) |
| AA/GG | 6 (4.6) | 3 (7.7) | 3 (3.3) | 10 (1.2) |
| n | 131 | 39 | 92 | 824 |
| Mean Age | 76.2 | 65.6 | 80.8 | 41.2 |
| | $\chi^2$ = 24.24673 | $\chi^2$ = 25.95232 | $\chi^2$ = 15.73515 | |
| | DF = 8 | DF = 8 | DF = 8 | |
| | p = 0.00208 | p = 0.00107 | p = 0.04633 | |

| PNMT (−387/−182) | ALL AD | EOAD | LOAD | Group II Controls |
|---|---|---|---|---|
| GG/AA | 3 (2.3) | 1 (2.6) | 2 (2.2) | 1 (0.9) |
| GG/AG | 13 (9.9) | 2 (5.1) | 11 (12.0) | 7 (6.0) |
| GG/GG | 18 (13.7) | 7 (17.9) | 11 (12.0) | 16 (13.8) |
| GA/AA | 8 (6.1) | 4 (10.3) | 4 (4.3) | 4 (3.4) |
| GA/AG | 24 (18.3) | 1 (2.6) | 23 (25.0) | 44 (37.9) |
| GA/GG | 8 (6.1) | 3 (7.7) | 5 (5.4) | 4 (3.4) |
| AA/AA | 38 (29.0) | 12 (30.8) | 26 (28.3) | 25 (21.6) |

TABLE 3-continued

| | | | | |
|---|---|---|---|---|
| AA/AG | 13 (9.9) | 6 (15.4) | 7 (7.6) | 12 (10.3) |
| AA/GG | 6 (4.6) | 3 (7.7) | 3 (3.3) | 3 (2.6) |
| n | 131 | 39 | 92 | 116 |
| Mean Age | 76.2 | 65.6 | 80.8 | 61 |
| | $\chi^2 =$ 14.3313 | $\chi^2 =$ 21.03942 | $\chi^2 =$ 7.50747 | |
| | DF = 8 | DF = 8 | DF = 8 | |
| | p = 0.07353 | p = 0.00704 | p = 0.48300 | |

Calculations for LOAD showed no significance ($\chi^2$=15.7; p=0.09266) when compared to the Group I controls, total control group ($\chi^2$=14.8; p =0.06) or Group II controls ($\chi^2$=7.5; p=0.483). When total AD patients were evaluated, significant differences were observed when compared to Group I controls ($\chi^2$=24.3; p=0.00416), but lost significance when compared to the total controls ($\chi^2$=23.6; p=0.00538) and Group II controls ($_{102}{}^2$=14.3; p=0.147).

Discussion: The present study indicates that two bi-allelic polymorphisms within the promoter of the PNMT gene independently show significant association with sporadic EOAD, and that when the genotypes of the two polymorphisms are combined, the double heterozygotes exhibit a marked decrease in the occurrence of EOAD. This further strengthens the possibility that both promoter markers are truly associated with EOAD and are not merely a result of linkage disequilibrium with another nearby marker. This also lends support to the hypothesis that any study that uses two independent markers not in linkage disequilibrium, in or around a gene of interest to assess the degree of association will prove to be more informative than studies that only use one marker to establish association (Comings and MacMurray, 2000). This technique may guard against the reporting of false positive results, since the association is dependent upon the independent interaction of two polymorphic markers with the disease being studied.

Recently, a promoter polymorphism of interleukin 1A (IL-1A) was reported (Grimaldi et al., 2000; Kehoe et al., 1999) and confirmed (Rebeck, 2000) as the first gene to show genetic association with sporadic EOAD. Hence, this makes our report of the PNMT gene only the second gene found to be associated with EOAD of the sporadic type. Of course, further independent analysis of the association reported here will be needed Furthermore, the results of this study suggest that it is likely that certain genotype combinations of the -387/-182 promoter markers alter the architecture of the PNMT gene. There may be changes at binding sites for specific transcription factors or interference with binding and/or function of the transcriptional machinery, thereby down-regulating the overall transcription of the PNMT gene. This is consistent with findings of Burke et al. (1987; 1988; 1990; 1994) which demonstrate that PNMT activity as well as the amounts of both protein and mRNA are reduced in AD patients. A similar genetic control and correlation between mRNA synthesis and enzyme levels were found in studies with inbred rat strains. Differential expression of the PNMT gene between Fischer 344 and Buffalo inbred rat strains has shown that Fischer 344 rats consistently express both more PNMT protein and mRNA than their Buffalo counterparts (Perry et al., 1983; Park et al., 1986; Evinger et al., 1994).

PNMT gene expression is also sensitive to control by other neurotransmitter systems. Evinger et al. have reported that cholinergic induced stimulation of both muscarinic and nicotinic receptors independently increases the production of PNMT mRNA (Evinger et al., 1994). Significant reductions in neurotransmitter activity related to the cholinergic system is best documented in patients with AD. Significant reductions in enzymatic activity of choline acetyltransferase (ChAT) have been reported in the hippocampus and amygdala, as well as many other prominent cortical (frontal, parietal, temporal) brain regions, with the most severe effects observed most often in younger, sporadic AD patients (Siek et al., 1990; Palmer et al., 1986; Emre et al., 1993; Boissiere et al., 1997; Reinikainen et al., 1988). One may speculate that genetic susceptibility to EOAD is a product of these combined effects, where reduced cholinergic induction of PNMT gene expression occurs concomitant with the inheritance of a specific PNMT promoter genotype combination that reduces PNMT mRNA expression to some threshold level.

Example 3

Analysis of PNMT Polymorphisms and Multiple Sclerosis

Subjects and Methods: All subjects examined in this study were non-Hispanic Caucasians. DNA was isolated from 108 brain samples, 38 male and 70 female patients, with a primary diagnosis of MS from the Human Neurological Research Specimen Bank at Los Angeles Veterans Affairs Medical Center, Los Angeles, Calif. The age distribution for MS cases had a range of 30–86, with a mean age of 57.2; the age at onset of MS ranged from 18–57, with a mean onset age of 34.2. DNA was obtained from blood leukocytes of control samples (n=774), consisting of three cohorts: (1) 163 adult students from a nearby university, 78 male and 85 female; (2) 36 non-obese female patients from Loma Linda University; and (3) 575 parents of twins from the Minnesota Twin and Family Study, 220 male and 355 female. The age range of controls was 23–66, with a mean of 42.5 years. All studies were approved by the IRB committees of the involved institutions and each subject signed a consent form.

PNMT genotyping: Two polymorphic loci in the promoter region of the PNMT gene were studied and evaluated as previously described. Briefly, both of the polymorphisms consist of a G to A transition at positions -387 and -182 with respect to the gene transcription start site. The two polymorphisms are separately PCR-amplified, cut with the appropriate restriction endonuclease, separated using PAGE, and visualized by ethidium bromide staining.

Statistical Methods: Alleles and genotypes were counted and their distributions between groups were determined. The Chi-square ($\chi^2$) test was employed to statistically compare these groups. When appropriate, a Bonferroni correction for multiple comparisons was made. Differences were considered significant at (p=0.05). Linkage disequilibrium was tested as described by Lynch and Walsh (1998). R-square estimates were calculated using multiple regression analysis. All statistical data calculations were done with the SPSS statistical package for Macintosh (release 6.1.1) (SPSS, Inc, Chicago, Ill.).

Results: The distribution of the PNMT G/A polymorphisms at position -387 and -182 are shown in Table 4. Additionally, the three control groups were examined for possible differences in allelic frequencies and genotype prevalence. No differences were observed between control groups. Furthermore, there were no observed differences between both male and female controls ($\chi^2$=14.44, p=0.07103) and between male and female MS ($\chi^2$=9.78, p=0.28082) cases. However, using the $\chi^2$ test, we calculated the statistical difference between subjects with MS vs. control subjects for both markers. We observed statistically significant increases in frequency of the GG genotype at the -387 marker ($\chi^2$=12.74, p=0.0017) and of the AA genotype at the -182 marker ($\chi^2$=6.10, p=0.0474) in MS patients. The data for the -387 marker suggest a very strong molecular heterosis effect, where the heterozygous genotype is under-represented in MS subjects when compared to either of the two homozygous genotypes(Comings and MacMurray, 2000). In addition, while the -387 GG homozygous genotype appears to confer increased risk to MS and the GA genotype appears to confer protection against MS, the AA genotype does not appear to contribute to disease progression at all. Based on these data, the degree of linkage disequilibrium (LD) between the two markers was of interest. Upon analysis, we observed that the G-387A and G-182A promoter polymorphisms are in incomplete LD (D=−0.18, SE=0.009) and appear to contribute differently to MS. Previously, we have reported that analysis of two polymorphisms within the same gene will be evaluated as though they are different genes as long as they are not in complete LD with one another (Comings et al., 2000). This suggested that further analysis of the interaction between the two markers might reveal an additive effect.

was a significant difference between the PNMT gene polymorphism distributions of patients with MS vs. control subjects ($\chi^2$=65.03, p=<0.00001). Evaluation of the genotype combinations in male patients with MS vs. male control subjects ($\chi^2$=36.09, p=0.00004) and female patients with MS vs. female control subjects ($\chi^2$=36.09, p=0.00002) were statistically significant. The PNMT GG/AA and GG/AG genotype combinations were found to be overly-represented in patients with MS (12.0% and 13.9%, respectively) when compared to controls (1.4% and 4.9%, respectively). Taken together, the presence of either the GG/AA or GG/GA genotype accounted for 25.9% of all MS patients, 24.3% being female and 29% being male, but only accounted for 6.3% of all controls (6.1% female and 6.7% male). An estimate of the upper limit of the percentage of the explained variance ($r^2$) between MS and control samples was calculated for the PNMT gene, revealing that the PNMT gene accounted for 5.5% of the variance between MS and controls.

TABLE 4

Patients with Multiple Sclerosis (MS) and Controls with the PNMT G (−387)/A (−387) and G (−182)/A (−182) Genotypes.

| PNMT | Genotype(−387), No. of Patients | | | Allele Frequency % | | Genotype(−182), No. of Patients | | | Alelle Frequency % | |
|---|---|---|---|---|---|---|---|---|---|---|
| | G | G/A | A | G | A | G | G/A | A | G | A |
| MS Subjects (n = 108) | 34 | 29 | 45 | 45 | 55 | 11 | 50 | 47 | 33 | 67 |
| Control Subjects (n = 774) | 149 | 328 | 297 | 40 | 60 | 152 | 343 | 279 | 42 | 58 |
| | | $\chi^2$ = 12.742 | | | | | $\chi^2$ = 6.0978 | | | |
| | | DF = 2 | | | | | DF = 2 | | | |
| | | P = 0.0017 | | | | | P = 0.0474 | | | |

The distributions of the polymorphic PNMT G-387A/G-182A genotype combinations are shown in Table 5. There

TABLE 5

Distribution of the PNMT −387/−182 Polymorphisms in Patients with MS and Controls.

| | MALE SUBJECTS | | FEMALE SUBJECTS | | TOTAL SUBJECTS | |
|---|---|---|---|---|---|---|
| PNMT (−387/−182) | MS | Control | MS | Control | MS | Control |
| GG/AA | 5 (13.2) | 2 (0.7) | 8 (11.4) | 9 (1.9) | 13 (12.0) | 11 (1.4) |
| GG/AG | 6 (15.8) | 18 (6.0) | 9 (12.9) | 20 (4.2) | 15 (13.9) | 38 (4.9) |
| GG/GG | 2 (5.3) | 45 (15.1) | 4 (5.7) | 55 (11.6) | 6 (5.6) | 100 (12.9) |
| GA/AA | 2 (5.3) | 16 (5.4) | 1 (1.4) | 28 (5.9) | 3 (2.8) | 44 (5.7) |
| GA/AG | 12 (31.6) | 96 (32.2) | 12 (17.1) | 145 (30.5) | 24 (22.2) | 241 (31.1) |
| GA/GG | 0 (0.0) | 16 (5.4) | 2 (2.9) | 27 (5.7) | 2 (1.9) | 43 (5.6) |
| AA/AA | 7 (18.4) | 73 (24.5) | 24 (34.3) | 151 (31.7) | 31 (28.7) | 224 (28.9) |
| AA/AG | 2 (5.3) | 25 (8.4) | 9 (12.9) | 39 (8.2) | 11 (10.2) | 64 (8.3) |
| AA/GG | 2 (5.3) | 7 (2.3) | 1 (1.4) | 2 (0.4) | 3 (2.8) | 9 (1.2) |
| n = | 38 | 298 | 70 | 476 | 108 | 774 |
| | $\chi^2$ = 36.08569 | | $\chi^2$ = 38.08324 | | $\chi^2$ = 65.0318 | |
| | DF = 8 | | DF = 8 | | DF = 8 | |
| | P = 0.00004 | | P = 0.00002 | | P = <0.00001 | |

Discussion: This study was launched primarily because genome scan data of MS patients from the UK (Sawcer et al., 1996; Chataway et al., 1999) and Finland (Kuokkanen et al., 1997) suggested that there exists a susceptibility factor near the region where PNMT has been shown to map, 17q21–q22. Additional evidence was provided by a genome scan for suceptibility loci in mice with experimental allergic encephalomyelitis (EAE), the predominant animal model of human MS. In this murine genome scan, EAE-susceptible mice (SJL/J-strain) were crossed with the relatively EAE-resistant mice (B10.S/DvTe-strain) in an effort to identify new loci and confirm previously identified susceptibility loci for EAE (Butterfield et al., 1998). Butterfield et al. (1998) identified a QTL locus, eae7, in which alleles were shown to be associated with shorter duration, but lesser severity, of the clinical signs of EAE. The eae7 locus maps to murine chromosome 11 in an area known to be syntenic with the human chromosome interval 17q11–q23.

Using these data, we evaluated the PNMT gene as a candidate for genetic susceptibility to MS. The data from our study suggest that two bi-allelic polymorphisms within the promoter of the PNMT gene, at positions -387 and -182, independently show statistically significant association with MS. Further analysis revealed that when the genotypes of the two polymorphisms are combined, both male and female subjects show statistically significant association with specific combinations when compared with the appropriate male and female controls. Although independent analysis revealed differences between the two polymorphisms in MS patients and controls, it is apparent from the p-values in Table 4 and the allele frequencies in Table 5 that the G allele of the 5–387 marker and the A allele of the -182 marker are likely to account for much of this association. This strengthens the possibility that both promoter markers are truly associated with MS and are not merely a result of linkage disequilibrium with another nearby marker (see Example 2). Furthermore, our data support the hypothesis that any study that uses two independent markers (SNPs) that are in only partial LD, in or around a gene of interest, to assess the degree of association will prove to be more informative than studies that only use one marker to establish association (Comings and MacMurray, 2000). This technique, when employed, may reduce the likelihood of reporting false positive results, since the association relies upon the independent interaction of two polymorphic markers with the disease being studied (see Example 2).

EAE studies have found that not all myelin-antigen (myelin basic protein, MBP) reactive CD4+ T-cell lines are able to induce the EAE phenotype (Benveniste, 1995). This suggests that genetic heterogeneity of T-cell populations influence the encephalithogenicity of these cells (Benveniste, 1995). Similarly, not all rat strains are equally susceptible to EAE. For instance, Lewis (LEW/N) rats show an increased likelihood for developing pro-inflammatory diseases from treatment with MBP-adjuvant when compared to Fischer rats (F344/N) which show some resistance (histocompatible) for developing EAE (Sternberg and Licinio, 1995). Some evidence suggests that differences at level of the genomic sequence level, particularly in regulatory regions of the gene (like the promoter), may contribute to these strain differences (Evinger et al., 1986).

A study by Perry et al. (1983) reports that Fischer 344 rats, when compared to Buffalo rats, show increases in PNMT activity from adrenomedullary and medulla-pons tissues of five- and four-times, respectively. Furthermore, they found an inverse relationship between brain PNMT activity and the density of brain alpha-adrenergic receptor density and suggest that an inherited difference in neuronal adrenergic function/dysfunction regulate the decreases seen in brain alpha-adrenergic receptor density.

Park and colleagues (1986) found that PNMT activity from rat brain and adrenals, two major sites of adrenergic cell populations, differs between four common laboratory rat strains, Fischer 344, Sprague-Dawley, Lewis, and Buffalo. Analysis of adrenomedullarly PNMT activity was found to be the highest in Fischer 344 rats (100% activity), followed by Sprague-Dawley (81%), Lewis (58%), and Buffalo (16%). However, PNMT activity from the medulla oblongata in the same animals was found to be very similar in the Fischer 344, Sprague-Dawley, and Lewis rat strains. Only Buffalo rats were found to have roughly half of the PNMT activity of that found in their Fischer 344 counterparts. Further analysis by this group found that the amount of PNMT enzyme protein and not the presence of inactive forms of the enzyme protein accounted for the differences seen in these two tissues (Evinger et al., 1986).

Similar studies were conducted with samples obtained from NIMH DNA bank for subjects with bipolar disorder (manic-depression), schizophrenia and ADHD. The results showed that the PNMT polymorphisms are also associated with these disorders.

The data from the studies described above demonstrate the association of PNMT polymorphisms and neurologic and neuropsychiatric diseases or disorders involving adrenergic neurons. The association of the risk for these disorders on the basis of the genotype of the individual is important in early identification of individuals as risk and for determining specific treatment modalities. The disclosed PNMT alleles can also be combined with other alleles associated with these disorders in a panel to assess the risk of the diseases. The data demonstrates the association of genotypes as detailed below.

For AD: The double heterozygote GA-387/AG-182 (also expressed as GA/AG) is negatively associated with EOAD with 2.6% in EOAD vs 37.9% in age matched controls. Thus, the double heterozygote is protective against EOAD. The genotypes that were associated with EOAD were the double homozygotes i.e. GG/AA (2.6% in EOAD vs 0.9% in control), GG/GG 17.9% in EOAD vs 13.8%), AA/AA (30.8% in EOAD vs 21.6% in control), and AA/GG (7.7% in EOAD vs 2.6% in control). In other words, doubly heterozygous individuals are at the lowest risk for Alzheimer's disease, whereas doubly homozygous individuals are at the highest risk for Alzheimer's disease.

For MS: The GG-387 genotype is associated with MS. This association is most marked when the -182 SNP is AA (GG/AA; 12% in MS vs 1.4% in control), and when the -182 SNP is AG (GG/AG; 13.95 MS vs 4.9% control), and reversed when the -182 SNP is GG (GG/GG; 5.6% MS vs 12.9% control). The only other genotypes showing a difference between MS and control was the GA-387/AG-182 (22.2% in MS vs. 31.1% in control). In other words, individuals which are doubly homozygous GG at -353 and AA or AG at -148 are at the highest risk for Multiple Sclerosis.

For bipolar and schizophrenia: The preliminary data shows that an increase in double heterozygosity is associated with manic depressive disorder and ADHD, and a decrease in double heterozygosity is associated with schizophrenia.

If there are two alleles at a polymorphism associated with a gene, and one allele (allele 1) is associated with a decrease in activity of that gene compared to allele 2, and a decrease in activity is associated with phenotype X, it would be anticipated what individuals with the 11 genotype would score highest for phenotype X, 12 individuals would be intermediate, and 22 individuals would score lowest. However, in many cases it is the 12 individuals who score the highest, while both the 11 and 22 individuals have lower scores. This counter-intuitive result is referred to heterosis. When it occurs at the level of an individual polymorphism, we refer it as molecular heterosis (Comings and MacMurray, 2000). Molecular heterosis is a situation where a trait is higher (positive heterosis) or lower (negative heterosis) in 12 heterozygotes than either the 11 or 22 homozygotes. We believe that the most logical explanation is that many physiological processes are inverted U shaped, such that too little is detrimental (11 genotype), too much is detrimental (22 genotype), and an intermediate level of a compound (12 genotype) is just right. We call this the Goldilocks effect, not too hot, not too cold, just right.

If a gene is assessed by using two SNPs that are only in partial linkage disequilibrium, positive or negative heterosis may be seen at both SNPs. Thus, a person who was a double heterozygote could be the most (or the least) affected. In the case of EOAD, double heterozygotes were rare while double homozygotes were common. If one were to make a phenotype score consisting of 1=AD and 0=no AD, that score would be low for heterozygotes at either SNP (single heterozygosity) and lowest for double heterozygotes, and thus this would be negative heterosis.

The invention having been described, it will be apparent to those skilled in the art that the same may be varied in many ways without departing from the spirit and scope of the invention. Any and all such modifications are intended to be included within the scope of the claims.

Bibliography

Altschul, S. F. et al. (1990). *J. Mol. Biol.* 215:403.
Altschul, S F, et al. (1997). *Nucl. Acids Res.* 25:3389–3402.
Anand, R (1992). *Techniques for the Analysis of Complex Genomes* (Academic Press).
Arango, V et al. (1988). *J Comp Neurol* 273:224–40.
Arnsten, A F T and Goldman-Rakic, P S (1985). *Science* 230:11273–1276.
Arnsten, A F T et al. (1996). *Arch. Gen. Psychiatry* 53:448–455.
Aston-Jones, G. (2000). In *Cognition, Emotion and Autonomic Responses,* Elsevier, Amsterdam.
Aston-Jones, G et al. (1984). In *Frontiers of Clin. Neurosci.* Vol 2., Williams and Williams, Baltimore, pp 91–116.
Aston-Jones, G, et al. (1986). *Science* 234:734–737.
Aston-Jones, G (1994). "Locus coeruleus, stress, and post traumatic stress disorder: Neurobiological and clinical parallels." In *Catecholamine Function in Post Traumatic Stress Disorder: Emerging Concepts,* American Psychiatric Press, pp. 17–64.
Aston-Jones, G, et al. (1996). *Progress in Brain Res.* 107:379–402.
Aston-Jones, G, et al. (1999). *Biol. Psychiatry* 46:1309–1320.
Ausubel, F M, et al. (1992). *Current Protocols in Molecular Biology,* (John Wiley & Sons, New York, N.Y.).
Axelrod, J and Weinshiboum, R (1972). *New Eng. J. Med.* 1972; 287:237–242.
Baetge, E E, et al. (1988). *Proceedings of the National Academy U.S.A.* 1988; 85:3648–3652.
Bartel, P L, et al. (1993). "Using the 2-hybrid system to detect protein-protein interactions." In *Cellular Interactions in Development: A Practical Approach,* Oxford University Press, pp. 153–179.
Beal, M F et al. (1986). *Ann. Neurology* 20:282–288.
Bell, J I and Lathrop, G M (1996). *Nat Genet.* 13:377–378.
Benveniste, E N (1995). In: *Human Cytokines: Their Role in Disease and Therapy.* Aggarwal, B B and Puri, R K (eds), Blackwell Science, Inc., Cambridge, Mass., pp. 195–214.
Betito, K, et al. (1994). *Am. J Physiology* 267:R212-R220.
*Biocomputing: Informatics and Genome Projects,* Smith, D. W., ed., Academic Press, Press, NY (1993).
Boissiere, F et al. (1997). *Neurosci Lett* 225:169–72.
Borman, S (1996). *Chemical & Engineering News,* December 9 issue, pp. 42–43.
Bunney, W E (1977). *Ann. Int. Med.* 87:319–335.
Burke, W J et al. (1987). *Ann. Neurol.* 22:278–280.
Burke, W J et al (1988). *Ann Neurol* 24:532–6.
Burke, W J et al. (1990). *J. Am. Geriatr. Soc.* 38:1275–1282.
Burke, W J et al. (1994). *Brain Res* 661:35–42.
Butterfield, R J et al. (1998). *J Immunol.* 161:1860–1867.
Capecchi, M R (1989). *Science* 244:1288.
Cariello, N F (1988). *Am. J. Human Genetics* 42:726–734.
Carli, M et al., (1983). *Behav. Brain Res.* 9:361–380.
Chan-Palay, V (1991). *Progress in Brain Res.* 88:625–630.
Chataway, J. et al. (1999). *J Neuroimmunol.* 98:208–213.
Chee, M, et al. (1996). *Science* 274:610–614.
Chevray, P M and Nathans, D N (1992). *Proc. Natl. Acad. Sci. USA* 89:5789–5793.
Comings, D E and MacMurray, J P (2000). *Mol Genet Metab.* 71:19–31.
Comings, D E et al. (2000). *Clin Genet.* 58:375–385.
Compton, J (1991). *Nature* 350:91–92.
*Computational Molecular Biology,* Lesk, A. M., ed., Oxford Univ. Press, NY (1988).
*Computer Analysis of Sequence Data,* Part I, Griffin, A. M., and Griffin, H. G., eds., Humana Press, NJ (1994).
Conner, B J, et al. (1983). *Proc. Natl. Acad. Sci. USA* 80:278–282.
Cotten, M, et al. (1990). *Proc. Natl. Acad. Sci. USA* 87:4033–4037.
Davies, P and Maloney, A J F (1976). *Lancet* 2:1403.
Davies, P et al. (1980). *Nature* 288:279–280.
DeRisi, J, et al. (1996). *Nat. Genet.* 14:457–460.
Deutscher, M (1990). *Meth. Enzymology* 182:83–89 (Academic Press, San Diego, Calif.).
Devereux, J et al. (1984). *Nucl. Acids Res.* 12:387.
Donehower, L A, et al. (1992). *Nature* 356:215.
Dyment, D A et al. (1997). *Hum Mol Genet.* 6:1693–1698.
Ebers, G C et al. (1986). *N Engl J Med.* 315:1638–1642.
Ebers, G C et al. (1995). *Nature.* 377:150–151.
Ebers, G C et al. (1996). *Nat Genet.* 13:472–476.
Editorial (1996). *Nature Genetics* 14:367–370.
Elghanian, R, et al. (1997). *Science* 277:1078–1081.
Emre, M et al. (1993). *J Comp Neurol* 336:117–34.
Evinger, M J et al. (1986). *Brain Res.* 387:63–73.
Evinger, M J et al. (1994). *J Neurosci* 14:2106–16.
Fahy, E, et al. (1991). *PCR Methods Appl.* 1:25–33.
Fei, Z. et al. (1998). *Nucleic Acids Res.* 26:2827–2828.
Fields, S and Song, O-K (1989). *Nature* 340:245–246.
Finkelstein, J, et al. (1990). *Genomics* 7:167–172.
Fodor, S P A (1997). *Science* 277:393–395.
Fu, D-J., et al. (1998). *Nat. Biotechnol.* 16:381–384.
Girardi, N L, et al. (1995). *Pediatr. Res.* 1995; 38:539–542.
Glover, D (1985). *DNA Cloning,* I and II (Oxford Press).
Goding (1986). *Monoclonal Antibodies: Principles and Practice,* 2d ed. (Academic Press, NY).
Godowski, P J, et al. (1988). *Science* 241:812–816.
Grimaldi, L M et al (2000). *Ann. Neurol.* 47:361–365.
Grompe, M (1993). *Nature Genetics* 5:111–117.
Grompe, M, et al. (1989). *Proc. Natl. Acad. Sci. USA* 86:5855–5892.

*Guide to Huge Computers,* Martin J. Bishop, ed., Academic Press, San Diego, Calif. (1994).
Guthrie, G and Fink G R (1991). *Guide to Yeast Genetics and Molecular Biology* (Academic Press).
Hacia, J G, et al. (1996). *Nature Genetics* 14:441–447.
Haines, J L et al. (1996). *Nat Genet.* 13:469–471.
Hanna, G L, et al. (1996). *Biol. Psychiatry* 40:553–555.
Harlow, E and Lane, D (1988). *Antibodies: A Laboratory Manual* (Cold Spring Harbor Laboratory, Cold Spring Harbor, N.Y.).
Haskó, G and Szabó, C (1998). *Biochem Pharmacol.* 56:1079–1087.
Hasty, P K, et al. (1991). *Nature* 350:243.
Hoehe, M R, et al. (1989a). *Nucleic Acids Res.* 17:828.
Hoehe, M R, et al. (1989b). *Nucleic Acids Res.* 17:2148.
Hoehe, M R et al. (1992). *Hum Mol Genet.* 1:175–178.
Homykiewicz, O. (1982). *Nature* 299:484.
Huse, W D, et al. (1989). *Science* 246:1275–1281.
Innis, M A, et al. (1990). *PCR Protocols: A Guide to Methods and Applications* (Academic Press, San Diego, Calif.).
Jablonski, E, et al. (1986). *Nucl. Acids Res.* 14:6115–6128.
Kalman, B and Lublin, F D (1999). *Biomed Pharmacother.* 53:358–370.
Kanehisa, M (1984). *Nucl. Acids Res.* 12:203–213.
Kehoe, P et al (1999). *Hum Mol Genet* 8 (2):237–45.
Kinszler, K W, et al. (1991). *Science* 251:1366–1370.
Klinteberg, B A and Magnusson, D (1989). *Eur. J. Personality* 1989; 3:81–93.
Kohler, G and Milstein, C (1975). *Nature* 256:495–497.
Kraemer, F B, et al. (1993). *J. Lipid Res.* 34:663–672.
Kuokkanen S, Gschwend M, Rioux J D, et al. Genomewide scan of multiple sclerosis in Finnish multiplex families. *Am J Hum Genet.* 1997;61(6):1379–1387.
Landegren, U, et al. (1988). *Science* 242:229–237.
Lee, J E, et al. (1995). *Science* 268:836–844.
Lipshutz, R J, et al. (1995). *BioTechniques* 19:442–447.
Lockhart, D J, et al. (1996). *Nature Biotechnology* 14:1675–1680.
Lynch, M and Walsh, B (1998). *Genetics and Analysis of Quantitative Traits,* Sinaure Associates, Inc, Sunderland, Mass.
Maniatis, T, et al. (1982). *Molecular Cloning: A Laboratory Manual* (Cold Spring Harbor Laboratory, Cold Spring Harbor, N.Y.).
Martin, R, et al. (1990). *BioTechniques* 9:762–768.
Matthews, J A and Kricka, L J (1988). *Anal Biochem.* 169:1.
Mefford, I N and Potter, W Z (1989). *Med Hypotheses* 29:33–42.
Merrifield, B (1963). *J. Am. Chem. Soc.* 85:2149–2156.
Mifflin, T E (1989). *Clinical Chem.* 35:1819–1825.
Modrich, P (1991). *Ann. Rev. Genet.* 25:229–253.
Mombaerts, P, et al. (1992). *Cell* 68:869.
Mumford, C J et al. (1994). *Neurology.* 44:11–15.
Newton, C R, et al. (1989). *Nuc. Acids Res.* 17:2503–2516.
Nguyen, Q, et al. (1992). *BioTechniques* 13:116–123.
Novack, D F, et al. (1986). *Proc. Natl. Acad. Sci. USA* 83:586–590.
Orita, M, et al. (1989). *Proc. Natl. Acad. Sci. USA* 86:2766–2770.
Palmer, A M et al. (1986). *Neurosci Lett* 66:199–204.
Park, D H et al. (1986). *Brain Res* 372:185–8.
Perry, B D et al. (1983). *Science* 221:1297–9.
Perry, E K et al. (1981). *J. Neurol. Sci.* 51:279–287.
Price, D L et al. (1998). *Annu Rev Genet* 32:461–93.
Philpott, K L, et al. (1992). *Science* 256:1448.
Pliszka, S R, et al. (1994). *J. Am. Acad. Child. Adolesc. Psychiatry.* 33:1165–1173.
Podulso, S E, et al. (1991). *Am. J Hum. Genet.* 49:106.
Rebeck, G W (2000). *Neurosci Lett* 293:75–7.
Reinikainen, K J et al. (1988). *Neurochem Res* 13:135–46.
*Remington's Pharmaceutical Sciences,* 18th Ed. (1990, Mack Publishing Co., Easton, Pa.).
Rigby, P W J, et al. (1977). *J. Mol. Biol.* 113:237–251.
Ruano, G and Kidd K K (1989). *Nucl. Acids Res.* 17:8392.
Sadovnick, A D et al. (1993). *Ann Neurol.* 33:281–285.
Sambrook, J, et al. (1989). *Molecular Cloning: A Laboratory Manual,* 2nd Ed. (Cold Spring Harbor Laboratory, Cold Spring Harbor, N.Y.).
Sara, S J et al. (1994). *Brain Res. Bull.* 35:457–465.
Sawcer, S et al. (1996). *Nat Genet.* 13:464–468.
Scharf, S J, et al. (1986). *Science* 233:1076–1078.
Scopes, R (1982). *Protein Purification: Principles and Practice,* (Springer-Verlag, NY).
*Sequence Analysis in Molecular Biology,* von Heinje, G., Academic Press (1987).
*Sequence Analysis Primer,* Gribskov, M. and Devereux, J., eds., M Stockton Press, NY (1991)
Sheffield, V C, et al. (1989). *Proc. Natl. Acad. Sci. USA* 86:232–236.
Shenk, T E, et al. (1975). *Proc. Natl. Acad. Sci. USA* 72:989–993.
Shinkai, Y, et al. (1992). *Cell* 68:855.
Shoemaker, D D, et al. (1996). *Nature Genetics* 14:450–456.
Siek, G C et al. (1990). *Biol Psychiatry* 27:573–80.
Siever, L J and Davis, K L (1985). *Am. J. Psychiatry* 142:1017–1031.
Snouwaert, J N, et al. (1992). *Science* 257:1083.
Spargo, C A, et al. (1996). *Mol. Cell. Probes* 10:247–256.
Steinman, L (2000). *Nat Med.* 6:15–16.
Sternberg, E M and Licinio, J (1995). *Ann N Y Acad Sci.* 771:364–371.
Synder, S H (1976). *Am. J. Psychiatry* 130:61–67.
Taylor, J. D. et al. (2001). *Biotechniques* 30:661–669.
Terry, R D and Davies, P (1980). *Ann. Rev. Neurosci.* 3:77–95.
Terry, R D and Katzman, R (1983). *Ann. Neurol.* 14:497–506.
Usher, M et al. (1999). *Science* 283:549–554.
Valancius, V and Smithies O (1991). *Mol. Cell Biol.* 11:1402.
Vizi, E S (1998). *Ann N Y Acad Sci.* 851:388–396.
Walker, G T, et al., (1992). *Nucl. Acids Res.* 20:1691–1696.
Wartell, R M, et al. (1990). *Nucl. Acids Res.* 18:2699–2705.
Weinberg, W. A. and Harper, C. R. (1993). *Neurol. Clin.* 11:59–78.
Wetmur, J G and Davidson, N (1968). *J. Mol. Biol.* 31:349–370.
White, M B, et al. (1992). *Genomics* 12:301–306.
White, R and Lalouel J M (1988). *Annu. Rev. Genet.* 22:259–279.
Wu, D Y and Wallace R B (1989). *Genomics* 4:560–569.
Wu, S and Comings, D E (1999). *Psychiatr Genet.* 9:187–188.
Yamamoto, T and Hirano, A (1985). *Ann. Neurology* 17:573–577.
EP 0332435.
EP 225,807.
EP 425,731A.
WO 90/07936.
WO 92/19195.
WO 94/25503.
WO 95/01203.
WO 95/05452.
WO 96/02286.

WO 96/02646.
WO 96/11698.
WO 96/40871.
WO 96/40959.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.

U.S. Pat. No. 4,486,530.
U.S. Pat. No. 4,683,195.
U.S. Pat. No. 4,683,202.
U.S. Pat. No. 4,816,567.
U.S. Pat. No. 4,868,105.
U.S. Pat. No. 5,270,184.
U.S. Pat. No. 5,409,818.
U.S. Pat. No. 5,455,166.
U.S. Pat. No. 5,550,050.
U.S. Pat. No. 5,800,998.
U.S. Pat. No. 5,837,492.
U.S. Pat. No. 5,891,628.

What is claimed is:

1. A method of determining a risk in an individual for a neurological or neuropsychiatric disorder, wherein said disorder is selected from the group consisting of, early onset Alzheimer's Disease, Multiple Sclerosis, bipolar disorder, schizophrenia and attention deficit hyperactivity disorder, which comprises determining the genotype of an individual by analyzing polymorphisms at nucleotide positions -387 and -182 of the PNMT gene and correlating the genotype with a predetermined risk for said disorder.

2. The method of claim 1, wherein said disorder is early onset Alzheimer's Disease and said predetermined risk for said disorder is the presence of double homozygotes at the nucleotide positions -387 and -182 of the PNMT gene.

3. The method of claim 1, wherein said disorder is Multiple Sclerosis and said predetermined risk for said disorder is the presence of double homozygote GG at the nucleotide position -387 in combination with AA or AG at the nucleotide position -182 of the PNMT gene.

4. The method of claim 1, wherein said disorder is schizophrenia and said predetermined risk for said disorder is the presence of a decrease in double heterozygosity at the nucleotide positions -387 and -182 of the PNMT gene.

5. The method of claim 1, wherein said bipolar disorder is manic-depression and said predetermined risk for said disorder is an increase in double heterozygosity at the nucleotide positions -387 and -182 of the PNMT gene.

6. The method of claim 1, wherein said disorder is attention deficit hyperactivity disorder and said predetermined risk for said disorder is an increase in double heterozygosity at the nucleotide positions -387 and -182 of the PNMT gene.

* * * * *

UNITED STATES PATENT AND TRADEMARK OFFICE
CERTIFICATE OF CORRECTION

PATENT NO. : 6,660,476 B2
DATED : December 9, 2003
INVENTOR(S) : Comings et al.

It is certified that error appears in the above-identified patent and that said Letters Patent is hereby corrected as shown below:

Column 3,
Line 4, "Benveriste" should read as -- Benveniste --; and
Line 38, "HomyKiewicz" should read as -- HornyKiewicz --.

Column 11,
Line 59, "$10^{-9}$" should read as -- $10^{-8}$ --.

Column 14,
Line 35, "Manrheim" should read as -- Mannheim --; and
Line 49, after "well as greater than" and before "nucleotides" insert -- 40 --.

Column 30,
Line 30, "($\geq 0.05$)" should read as -- ($p \leq 0.05$) --.

Column 33,
Line 19, "($_{10z}Z=14.3; p=0.147$)" should read as -- ($X^2 = 14.3; p=0.147$) --.

Column 37,
Line 32, "5-387" should read as -- -387 --.

Column 41,
Line 16, "HomyKiewicz" should read as -- HornyKiewicz --.

Signed and Sealed this

First Day of June, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 4174
<212> TYPE: DNA
<213> ORGANISM: Homo sapiens
<220> FEATURE:
<221> NAME/KEY: misc_feature
<222> LOCATION: (1958)..(2159)
<223> OTHER INFORMATION: exon
<221> NAME/KEY: misc_feature
<222> LOCATION: (3159)..(3366)
<223> OTHER INFORMATION: exon
<221> NAME/KEY: misc_feature
<222> LOCATION: (3480)..(3915)
<223> OTHER INFORMATION: exon
<221> NAME/KEY: misc_feature
<222> LOCATION: (1935)..()
<223> OTHER INFORMATION: transcription start site

<400> SEQUENCE: 1

```
gaattcatgc cccagcacc ctctgttagt gccgcaataa atgctcaatc atgtgccaga      60
gttgcatctc tttccttgtg gttgggggg ctggccatgg gtgtccctc aatgccactt     120 ctgggaccag gctccgcatc tgagctaaat atggcagagt aatgggtaca ccccatactt    180
ggggtggggg tggggcagg aagagcttgt aaacagggtg ctgtctccag tctccttccc     240
gtaccctgac cgctgcccag tcctggcttc tgtgtccagc cccctggcac tgggtgggta    300
accagcaagc cagctggcat ccgcatccag ggtttgtttc aatgatgtct cgtggagaat    360
atggaggggc tggtgccagg actgtccttg gctttgctcg gggtgtgaac ggggtcagtg    420
acctctaaaa ctaacctgcc tctcagttct gaatccagac agaatcaatc ctcagctgtg    480
tctcgctcca caccccctgc cctggaagcc agggaaggtt ggaggtgcta gggggtcagg    540
ctcccctctg tgacccctgc agctgttgtg gtgactcatg tcccaaccta gctgcctctc    600
ccaaggagac tttcccctgg ggacaagggg gagggaatgc catggaggag gcccacatca    660
agcggggcca ggaacccacg gtggcaggag ctgggctggt gacctaccca ggcagaagg     720 gcccgggact catccagagg ggaaggaagg ggtcttcagg aagaccacgg agatgcccac    780
aggcagaatt ggcttcccat ctgggagata ggtggggaga ccctggcatt tttgacagcc    840
agaacctggg gtgctgagca gaatcttcat gcctggcctg gccgctcctt cggagggaag    900
ctggagggtg ggctgcgaga ggagtgggt caagagcccc tacatcgcag gaccccaaat     960
cggctgggcc ccaaggcgga ctgcgctccc cggtggcccc ggcggccctc cgcgaatggt   1020
cctgcccctc ccctgcccaa gccctctgcc ctcaccgggg tccggcgcgc cccgaagtgg   1080
cgggaacaac ccgaacccga accttctgtc ctggagcccc ccagataagc ggctgggaac   1140
```

-continued

```
ccgcggggcc cgcagggagg cccggctgtt ccgcccgtaa gtgcattaga agtacctccc    1200
tatgcgctgc atggagggag tgcggcctgc ttggggcccc ggagcgacca agcggagcgg    1260
aggccggaac ggactgtcct ttctggggcg gggtggggag ggggtgtcgc tggagggccc    1320
ggtggcatag caacggacga gagaggcctg gaggaggggc ggggaggggg agttgtgtgg    1380
cagttctaag ggaagggtgg gtgctgggac gggtgtccgg gagggagggg agcctggcgg    1440
ggtctggggc ctcgtcgcgg agggcgctgc gaggggaaaa ctggggaaag gcctaattc     1500 cccagtctcc acctcgaatc aggaaagaga aggggcgggc tgctgggcaa aagaggtgaa    1560
tggctgcggg gggctggaga agagagatgg gaggggccgg ccggcggggg tgaggggtc     1620 taaagattgt gggggtgagg aactgagggt ggggggcgcc cagaggcggg actcggggcg    1680
gggcaggcga ggcggagggc gagggctgcg ggacaagtac ggagccgggg gtgtggggga    1740
cgattgccgc tcgagccgcc gccccactca cctccggtgt gtctgcagcc cggacactaa    1800
gggagatgga tgaatgggtg gggaggatgc ggcgcacatg gccccgggcg gctcggcggt    1860
cagctgccgc ccccacagcg gaccggtcgg ggcggggtc gggcggtaga aaaaagggcc     1920
gcgagcgagc gggcactggg cggaccgcgg cggcagcatg agcggcgcag accgtagccc    1980
caatgcgggc gcagcccctg actcggcccc gggccaggcg gcggtggctt cggcctacca    2040
gcgcttcgag ccgcgcgcct acctccgcaa caactacgcg ccccctcgcg gggacctgtg    2100 caaccccgaac ggcgtcgggc cgtggaagct gcgctgcttg gcgcagacct tcgccaccgg   2160 tgagcgggg aaactgaggc acgagggaca agaggtcgtc ggggagtgaa agcaggcgca    2220
gggaaataaa aagaaggaaa gggagacaga cccaggccgc ctaacagatg gggaccaaga    2280
aacaagagat agctgagagg tgcaaacaga agagaaaaag gagcaacatc ccttaggaga    2340
ggggcagagg agagagaggt gagagagggg gcggagagtc tcagaattga gagctaaggt    2400
gggatcagga caactaggtg agatgctcag aattgagagc taaggtgggg ggaatgcagg    2460
acagactgag gtggagatgc ataggaggaa atgaggcaga tgtgggacag gggtgagaaa    2520
ctgccaggat ttcgtcgctg agcctggctg gtaggtatag ttgttttctt tcttttcttt    2580 tattttatt tcatttattt acttatttt atttttatt tgttttgaga cggcagtttc      2640
gctcttgttg cccaggctgg agtacaatgg ccgccatctc ggctcactgc aacctccgcc    2700
tccccggttc aagcgattct cttgcctcag cttcctagta gctgggatta cagcatgcgc    2760
ccccaatgcc tggctaattt atttgtattt ttagtagaga cgggacttct ccatgttggt    2820
caggctggtc tcgaactccc aaccttagga tccaccccacc ccggcctccc aaagtgctgg    2880
gattacaggt gtgagccact gcgcccggcc agtagtatag tcttctagat gtgaaacctg    2940
agtctcaaga gcggtgaagt tcccttccga agggcagccc atgttggagc tgggttcagt    3000
ctaactctgg ggccaatgct ttttccagat ggagacacat ttgcagagga gaaggaagaa    3060
ctagagagag gcagggagat gcagggagg gaagggtaag gaggcagggg ctgcctgggc     3120
tggctggcac caggaccctc ttcctctgcc ctgcccaggt gaagtgtccg gacgcaccct    3180
catcgacatt ggttcaggcc ccaccgtgta ccagctgctc agtgcctgca gccactttga    3240
ggacatcacc atgacagatt tcctggaggt caaccgccag gagctggggc gctggctgca    3300
ggaggagccg ggggccttca actggagcat gtacagccaa catgcctgcc tcattgaggg    3360
caaggggtaa ggactggggg gtgagggttg ggaggaggct tcccatagag tggctggttg    3420
gggcaacaga ggcctgagcg tagaacagcc ttgagccctg ccttgtgcct cctgcacagg    3480
```

-continued

```
gaatgctggc aggataagga gcgccagctg cgagccaggg tgaaacgggt cctgcccatc      3540
gacgtgcacc agcccagcc cctgggtgct ggagcccagg ctcccctgcc tgctgacgcc       3600
ctggtctctg ccttctgctt ggaggctgtg agcccagatc ttgccagctt tcagcgggcc      3660
ctggaccaca tcaccacgct gctgaggcct gggggcacc tcctcctcat cggggccctg       3720
gaggagtcgt ggtacctggc tggggaggcc aggctgacgg tggtgccagt gtctgaggag      3780
gaggtgaggg aggccctggt gcgtagtggc tacaaggtcc gggacctccg cacctatatc      3840
atgcctgccc accttcagac aggcgtagat gatgtcaagg gcgtcttctt cgcctgggct      3900
cagaaggttg ggctgtgagg gctgtacctg gtgccctgtg gccccaccc acctggattc       3960 cctgttcttt gaagtggcac ctaataaaga aataataccc tgccgctgcg gtcagtgctg      4020
tgtgtgctct cctggaagca gcaaggccag agatctgagt gtccgggtag gggagacatt      4080
caccctaggc tttttttcca gaagcttcct tgaggctagc attctgtacc actcattctt      4140
cccaaactaa ggaaggccaa ggtcagggga gctc                                 4174
```

<210> SEQ ID NO 2
<211> LENGTH: 282
<212> TYPE: PRT
<213> ORGANISM: Homo sapiens

<400> SEQUENCE: 2

```
Met Ser Gly Ala Asp Arg Ser Pro Asn Ala Gly Ala Ala Pro Asp Ser
 1               5                  10                  15

Ala Pro Gly Gln Ala Ala Val Ala Ser Ala Tyr Gln Arg Phe Glu Pro
            20                  25                  30

Arg Ala Tyr Leu Arg Asn Asn Tyr Ala Pro Pro Arg Gly Asp Leu Cys
        35                  40                  45

Asn Pro Asn Gly Val Gly Pro Trp Lys Leu Arg Cys Leu Ala Gln Thr
    50                  55                  60

Phe Ala Thr Gly Glu Val Ser Gly Arg Thr Leu Ile Asp Ile Gly Ser
65                  70                  75                  80

Gly Pro Thr Val Tyr Gln Leu Leu Ser Ala Cys Ser His Phe Glu Asp
                85                  90                  95

Ile Thr Met Thr Asp Phe Leu Glu Val Asn Arg Gln Glu Leu Gly Arg
            100                 105                 110

Trp Leu Gln Glu Glu Pro Gly Ala Phe Asn Trp Ser Met Tyr Ser Gln
        115                 120                 125

His Ala Cys Leu Ile Glu Gly Lys Gly Glu Cys Trp Gln Asp Lys Glu
    130                 135                 140

Arg Gln Leu Arg Ala Arg Val Lys Arg Val Leu Pro Ile Asp Val His
145                 150                 155                 160

Gln Pro Gln Pro Leu Gly Ala Gly Ala Gln Ala Pro Leu Pro Ala Asp
                165                 170                 175

Ala Leu Val Ser Ala Phe Cys Leu Glu Ala Val Ser Pro Asp Leu Ala
            180                 185                 190

Ser Phe Gln Arg Ala Leu Asp His Ile Thr Thr Leu Leu Arg Pro Gly
        195                 200                 205

Gly His Leu Leu Leu Ile Gly Ala Leu Glu Glu Ser Trp Tyr Leu Ala
    210                 215                 220

Gly Glu Ala Arg Leu Thr Val Val Pro Val Ser Glu Glu Val Arg
225                 230                 235                 240

Glu Ala Leu Val Arg Ser Gly Tyr Lys Val Arg Asp Leu Arg Thr Tyr
                245                 250                 255
```

-continued

```
Ile Met Pro Ala His Leu Gln Thr Gly Val Asp Asp Val Lys Gly Val
            260                 265                 270

Phe Phe Ala Trp Ala Gln Lys Val Gly Leu
        275                 280

<210> SEQ ID NO 3
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 3
cgggacaagt acggagcc                                                 18

<210> SEQ ID NO 4
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 4
ccatctccct tagtgtcc                                                 18

<210> SEQ ID NO 5
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 5
gtctccacct cgaatcag                                                 18

<210> SEQ ID NO 6
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 6
ccatctctct tctccagc                                                 18
```